(12) United States Patent
Forslund et al.

(10) Patent No.: US 8,560,068 B2
(45) Date of Patent: Oct. 15, 2013

(54) MEDICAL DEVICE FOR STIMULATION OF THE HIS BUNDLE

(75) Inventors: Mikael Forslund, Stockholm (SE); Johan Eckerdal, Knivsta (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 12/808,190

(22) PCT Filed: Dec. 18, 2007

(86) PCT No.: PCT/SE2007/001122
§ 371 (c)(1),
(2), (4) Date: Aug. 30, 2010

(87) PCT Pub. No.: WO2009/078751
PCT Pub. Date: Jun. 25, 2009

(65) Prior Publication Data
US 2010/0318147 A1    Dec. 16, 2010

(51) Int. Cl.
*A61N 1/00* (2006.01)
(52) U.S. Cl.
USPC ............................................................ 607/9
(58) Field of Classification Search
USPC ........................................................... 607/9
See application file for complete search history.

(56) References Cited

U.S. PATENT DOCUMENTS

| | | | |
|---|---|---|---|
| 5,545,201 A | 8/1996 | Helland et al. | |
| 6,609,027 B2 | 8/2003 | Kroll et al. | |
| 7,177,704 B2 | 2/2007 | Laske et al. | |
| 2002/0169484 A1 | 11/2002 | Mathis et al. | |
| 2003/0078625 A1* | 4/2003 | Casavant | 607/9 |
| 2003/0083727 A1 | 5/2003 | Casavant et al. | |
| 2004/0064158 A1 | 4/2004 | Klein et al. | |
| 2004/0064176 A1 | 4/2004 | Min et al. | |
| 2006/0247702 A1 | 11/2006 | Stegemann et al. | |

OTHER PUBLICATIONS

"Septal His-Purkinje Ventricular Pacing in Canines: A New Endocardial Electrode Approach," Karpawich et al., PACE, vol. 15 (1992) pp. 2011-2015.
"Excitation of the Intrinsic Conduction System Through His and Interventricular Septal Pacing," Laske et al. PAVE, vol. 29 (2006), pp. 397-405.
"Permanent, Direct His-Bundle Pacing: A Novel Approach to Cardiac Pacing in Patients With Normal His-Purkinje Activation," Deshmukh et al., Circulation, vol. 101 (2000) pp. 869-877.
Pervenous Pacing of the Specialized Conducting System in Man: His Bundle and A-V Nodal Stimulation, Narula et al., Circulation, vol. 41 (1970) pp. 77-87.

* cited by examiner

*Primary Examiner* — George Manuel (57) ABSTRACT

An implantable medical system for delivering pacing pulses to HIS bundle of a heart of a patient when implanted in said patient includes a medical lead, which is adapted to be attached with a distal end to tissue of said heart, including a at least two electrodes arranged being electrically separated from each other. The implantable medical device connectable to the medical lead includes a pacing circuit adapted to deliver the pacing pulses to said heart via the medical lead, a selection device connected between the pacing circuit and the electrodes adapted to selectively activate at least one of said electrodes, and a processing device adapted to control the selection device to selectively activate at least one of the electrodes to direct the pacing pulses to the HIS bundle.

22 Claims, 6 Drawing Sheets

MEDICAL DEVICE FOR STIMULATION OF THE HIS BUNDLE

BACKGROUND OF THE INVENTION

1. Field of the Invention

The present invention generally relates to an implantable medical system including an implantable medical device and an implantable medical lead for pacing the HIS Bundle.

2. Description of the Prior Art

Many studies have recently demonstrated the potential detrimental effects of RV (Right Ventricular) apex pacing. The stimulation of the ventricles through RV apex generates an activation pattern similar to LBBB (Left Bundle Branch Block) patients, with unsynchronized right and left ventricles as a result. The long term effects of RV apical pacing are thought to be (in the worst case) advancing CHF (Cardiac Heart Failure) or compromised hemodynamics.

One way to overcome these disadvantages is to implant a CRT (Cardiac Rhythm Therapy) system with a LV (Left Ventricular) that can restore the synchronization between the left ventricle and the right ventricle. However, for those patients which have an intact conduction system below the AV-node, pacing in upper regions in the RVOT/RV septal wall—or more beneficial—the Bundle of HIS, may restore synchronization as well.

Pacing in HIS Bundle may actually generate EGM's being more or less identical with the intrinsic or native ones. The pacing signal is propagated along the Purkinje fiber system and the patient will benefit from having a true physiologic pacing. However, pacing of the HIS Bundle area is difficult to achieve and/or optimize. It is a small area located deep in the tissue between the RA (Right Atrium) and RV, near the membranous septum or the interventricular septum. In addition, the depth at which the intrinsic conduction system lies is individual to every person.

Due to the fact that the Bundle of HIS is a structure located deep within the myocardium, the positioning of the medical lead must be optimized in three dimensions. Typically, the Bundle of HIS is reached from the atrium by mapping in the area of the Triangle of Koch. The correct region at which the endocardium should be penetrated with the lead in order to reach the Bundle of HIS is identified by finding the spot where the largest HIS Bundle potential is measured. The lead helix is then fixated in this spot.

However, studies have revealed that both the capture threshold and the sense thresholds as well as the ability to distinguish the signal from the HIS Bundle with the implantable lead is to a high degree dependent on the depth of the electrode (i.e. the helix) in the tissue, see, for example, Deshmukh et al., Circulation 2000; 101; 869-877 and Laske et al., PACE 2006; 29; 397-405. With a conventional lead, which has a length of the helix of approximately 1.5-2.0 mm, the helix may in some cases never reach the optimal site. In order to reach the desired spot in close proximity to the bundle of HIS, a longer helix will be required. This has been studied in Karpawich et al., PACE, Part II, 1992; 15; 2011-2015, where a helix having a length of 4.5 mm was used to pace HIS Bundle. A long conductive helix is however associated with negative side effects. For example, the depolarization of the tissue may become indistinctive relative the Bundle of HIS and a large conductive surface area of the helix will entail a reduced impedance.

In U.S. Pat. No. 7,177,704, a medical lead including a helix for pacing HIS Bundle is shown. The helically shaped electrode is partially masked with an insulative material, leaving an intermediate area unmasked and electrically conductive to allow for pacing at specific depths within the heart tissue. During the implantation, the physician rotates the electrode in and out of the tissue to determine an optimal position in which to pace the portion of the intrinsic conductive system. Since the depth at which the intrinsic system lies is different for every person, the physician rotates the helical electrode in and out of the tissue to determine an optimal conductive position. Consequently, the implantation procedure of the medical lead according to U.S. Pat. No. 7,177,704 may be cumbersome and time-consuming.

Thus, there is still a need within the art for an improved implantable medical device and an implantable medical lead capable of providing a reliable and accurate pacing of the His Bundle. There is also a need within the art of an improved implantable medical device and an implantable medical lead for stimulation of the His Bundle that can be implanted in an efficient way.

SUMMARY OF THE INVENTION

Thus, an object of the present invention is to provide an improved medical system, implantable medical device and medical lead capable of stimulating the heart of a patient such that a substantially native-like response can be achieved.

Another object of the present invention is to provide an improved medical system, implantable medical device and medical lead capable of delivering a reliable and accurate pacing of His Bundle.

A further object of the present invention is to provide an improved medical system, implantable medical device and medical lead for stimulation of His Bundle that can be implanted in a swift and efficient way.

Yet another object of the present invention is to provide an improved medical system, implantable medical device and medical lead for stimulation of His Bundle that enables an efficient post-implant optimization of the stimulation electrode position without the need of intervention.

According to an aspect of the present invention, there is provided a medical system for delivering pacing pulses to the HIS bundle of a heart of a patient when implanted in the patient or during an implantation procedure. The system includes at least one medical lead, which is adapted to be attached with a distal end to tissue of the heart, the medical lead including a lead body including a flexible insulating tubing and at least one conductor arranged within the tubing, a penetrating electrode arrangement in the distal end for enabling attachment of the lead to tissue, and at least two electrodes arranged on the electrode arrangement being electrically separated from each other, each being connected to the at least one conductor. The system also has a selection device connected to the electrodes and being adapted to selectively activate at least one of the electrodes. Furthermore, the system has an implantable medical device connectable to the medical lead, the medical device having a pacing circuit adapted to deliver the pacing pulses to the heart via the selection device, the medical lead and the at least one activated electrodes.

According to a second aspect of the present invention, there is provided a method for delivering pacing pulses to the HIS bundle of a heart of a patient. The method includes delivering pacing pulses to the heart via a medical lead adapted to be attached with a distal end to tissue of the heart, wherein the medical lead has a lead body including a flexible insulating tubing and at least one conductor arranged within the tubing, a penetrating electrode arrangement in the distal end for enabling attachment of the lead to tissue, and at least two electrodes arranged on the electrode arrangement being electrically separated from each other, each being connected to the at least one conductor.

According to another aspect of the present invention, there is provided a medical lead connectable to a medical system for delivering pacing pulses to the HIS bundle of a heart of a patient when implanted in the patient or during an implantation procedure of the lead from an implantable medical device of the medical system. The medical lead includes a lead body including a flexible insulating tubing and at least one conductor arranged within the tubing, a penetrating electrode arrangement in the distal end for enabling attachment of the lead to tissue, at least two electrodes arranged on the electrode arrangement being electrically separated from each other, each being connected to the at least one conductor, wherein the at least one electrode can be selectively activated to direct the pacing pulses to the HIS bundle.

According to a further aspect of the present invention, there is provided an implantable medical device for delivering pacing pulses to the HIS bundle of a heart of a patient when implanted in the patient or during an implantation procedure of the device, which device is connectable to a medical lead being adapted to be attached with a distal end to tissue of the heart, which medical lead includes a lead body including a flexible insulating tubing and at least one conductor arranged within the tubing, a penetrating electrode arrangement in the distal end for enabling attachment of the lead to tissue, at least two electrodes arranged on the electrode arrangement being electrically separated from each other, each being connected to the at least one conductor. Furthermore, the implantable medical device has a pacing circuit adapted to deliver the pacing pulses to the heart via the medical lead.

The present invention, in contrast to ventricular pacing, is based on pacing or stimulation at the HIS bundle, for example, low in atrial septum or high in the interventricular septum being similar to natural or intrinsic stimulation since depolarization in that case comes via the Purkinje system and subsequently spreads rapidly across the ventricle with more efficient heartbeats as a result. In Circulation, Journal of the American Heart Association, 1970; 41; 77-87, it is, for example, shown that during pacing at the HIS bundle, the QRS complex is identical to that during normal sinus rhythm. This is due to that induced (or spontaneous) pulses arising from HIS bundle are normally transmitted through the same pathways to the ventricular musculature producing similar patterns of ventricular depolarization. On the other hand, direct stimulation of the ventricular musculature or the right bundle branch produces aberrant QRS complex due to alteration in ventricular activation pattern from that during normal sinus rhythm. In order to make use of these findings the present invention is based on the idea of providing a medical lead with a penetrating electrode arrangement in the distal end including a number of electrodes located at different positions that can be selectively activated to stimulate tissue at different depths and locations. Thereby, the implantation procedure can be improved and can be made more swift and efficient with regard to, for example, time-consumption in comparison to the normal procedure due to the fact that the electrode can be attached to tissue (penetrate the endocardium) and that the physician thereafter may select the electrode providing the best HIS bundle stimulation. Moreover, the lead may also be used to adapt for morphological changes in the patient, for example, during a follow-up at the physician and an optimization (a selection of which electrode to be used for stimulation) can be performed to adapt for specific circumstances, for example, evolvement of fibrous capsule around the lead tip or lead migration/maturation. For example, the implantable medical device can be reconfigured to utilize another electrode more distal or more proximal to the first one. The system or medical device may also be adapted to automatically adapt for morphological changes in the patient and an optimization (a selection of which electrode to be used for stimulation) can be performed to adapt for specific circumstances, for example, evolvement of fibrous capsule around the lead tip or lead migration/maturation.

In one embodiment of the present invention, the medical device includes a processing device adapted to control the selection device to selectively activate at least one of the electrodes to direct the pacing pulses to HIS bundle. The processing device thus controls the selection device to selectively activate one or more electrode, which can be performed to optimize the stimulation at implantation, either automatically or upon instruction from the physician e.g. via an external programmer device, at regular intervals or continuously during operation of the implantable medical device to adapt for morphological changes in the patient or, for example, during a follow-up at the physician and an optimization (a selection of which electrode to be used for stimulation) can be performed to adapt for specific circumstances, for example, evolvement of fibrous capsule around the lead tip or lead migration/maturation using, for example, surface ECG signals. Hence, the electrode usage can be adjusted if inferior pacing characteristics upon lead migration or micro dislodgement appear when implanted, for example, in a chronic setting. For example, the implantable medical device can be reconfigured to utilize another electrode more distal or more proximal to the first one.

According to another embodiment, the selection device can be controlled manually. Thereby, a physician may, for example, during a follow up or during an implantation control the selection device to selectively activate one or more electrode.

In one embodiment, the medical system includes an extracorporeal programmer device adapted to control the selection device or the processing circuit to selectively activate one or more electrode. A physician may, in turn, provide the programmer device with instructions or the programmer device may automatically control the selection device to selectively activate one or more electrode. The programmer device may communicate with the implantable medical device wirelessly or via a physical connection.

In embodiments of the present invention, the programmer device further has a processing device adapted to control the selection device to selectively activate at least one of the electrodes to direct the pacing pulses to HIS bundle, the processing device is adapted to control the selection device to selectively activate at least one of the electrodes by connecting the at least one electrode with the pacing circuit based on at least one selection parameter.

In an embodiment of the present invention, the programmer device is adapted to obtain ECG or IEGM signals corresponding to a physiological activity of the heart and/or measurement signals corresponding to the operation of the electrodes. The IEGM signals corresponding to a physiological activity of the heart and/or measurement signals corresponding to the operation of the electrodes can be obtained from a measurement circuit of the medical device.

Thereby, the different electrodes of the medical lead can be evaluated based on physiological or hemodynamic activity of the heart and/or the functioning or operation of the electrodes. For example, the evaluation can be based on ECG or IEGM signals, a pace-ventricular interval, a sense-ventricular interval, capture thresholds and/or sense thresholds. During an implantation, the evaluation results or evaluation measures can be displayed on an external programmer device thereby allowing a physician performing the implantation to continuously monitor the evaluation results. The results can be transferred wirelessly or via a physical connection to the programmer device from the implantable medical device or the medical lead. Furthermore, when implanted, the measurement circuit may continuously or at regular intervals determine evaluation results. These results can be used to optimize the electrode location, i.e. change stimulation electrode, after implantation. The results may also be transferred to an external programmer device, whereby a physician may be informed that a post-implant optimization should be performed or has been performed.

In an embodiment of the present invention, the processing device is adapted to determine the at least one selection parameter based on an evaluation of the obtained IEGM signals and/or the measurement signals, which thus may be used for an optimization as described above.

In accordance with a further embodiment of the present invention, the electrodes, during a test procedure, are activated according to a predetermined scheme, the selection parameter(-s) obtained during a pacing period for each respective electrode is(are) evaluated to determine which electrode to use for the HIS bundle pacing, and the selection circuit is instructed to activate the determined electrode for HIS bundle pacing. This test procedure can be automatically performed at regular intervals or upon receiving an instruction from, for example, a physician via an external programmer device to adapt, for example, morphological changes in the patient or if inferior pacing characteristics upon lead migration or micro dislodgement appear when implanted, i.e. in the chronic setting. By automatically performing the test procedure at regular intervals, morphological changes in the patient or inferior pacing characteristics upon lead migration or micro dislodgement can be detected and compensated for at an early stage.

According to a further embodiment of the present invention, a conduction time from sensing a native event at the bundle of HIS or from a delivery of at least one pacing pulse to the HIS bundle to the subsequent ventricular activation is determined using surface ECG signals or IEGM signals and/or measurement signals corresponding to the operation of the electrodes. The selection circuit is instructed to initiate the test procedure if the determined conduction time exceeds a predetermined reference threshold. The reference threshold may be a recorded reference conduction time for the patient corresponding to the period of time from sensing a native event at the bundle of HIS or from a delivery of at least one pacing pulse to the HIS bundle to the subsequent ventricular activation can be determined.

In another alternative embodiment of the present invention, a morphology of the QRS complex, including the amplitude, and/or configuration, and/or duration, is determined for respective consecutive cardiac events using the measurement sensing signals corresponding to the physiological activity, the determined QRS complex is evaluated to determine whether it satisfies predetermined conditions, for example a predetermined reference QRS complex, and the selection circuit is instructed to initiate the test procedure if the determined QRS complex do not satisfies the predetermined conditions. The predetermined conditions may be a recorded reference QRS complex for the patient. The morphologies of the reference QRS complex may be compared to the measured QRS complex and if any substantial deviation is detected, for example, in amplitude of the R-wave, duration of the QRS complex, and/or configuration of the complex.

In alternatives of the present invention, the selection device is arranged in a medical lead or in the implantable medical device.

In one embodiment of medical lead the penetrating electrode arrangement includes a rotatable helix adapted for enabling an attachment of the lead to tissue by screwing the helix into the tissue, the helix comprising the at least two electrodes. In another embodiment of the medical lead the penetrating electrode arrangement includes a rotatable helix adapted for enabling an attachment of the lead to tissue by screwing the helix into the tissue and an penetrating pin comprising the at least two electrodes, the penetrating pin being arranged such that the helix partly encircles the pin.

As will be apparent to those of skill in the art, steps of the methods according to the present invention, as well as preferred embodiments thereof, are suitable to realize as computer program or as a computer readable medium.

Further objects and advantages of the present invention will be discussed below by means of exemplifying embodiments.

DESCRIPTION OF THE PREFERRED EMBODIMENTS

The following is a description of exemplifying embodiments in accordance with the present invention. This description is not to be taken in limiting sense, but is made merely for the purposes of describing the general principles of the invention.

Figure 1:
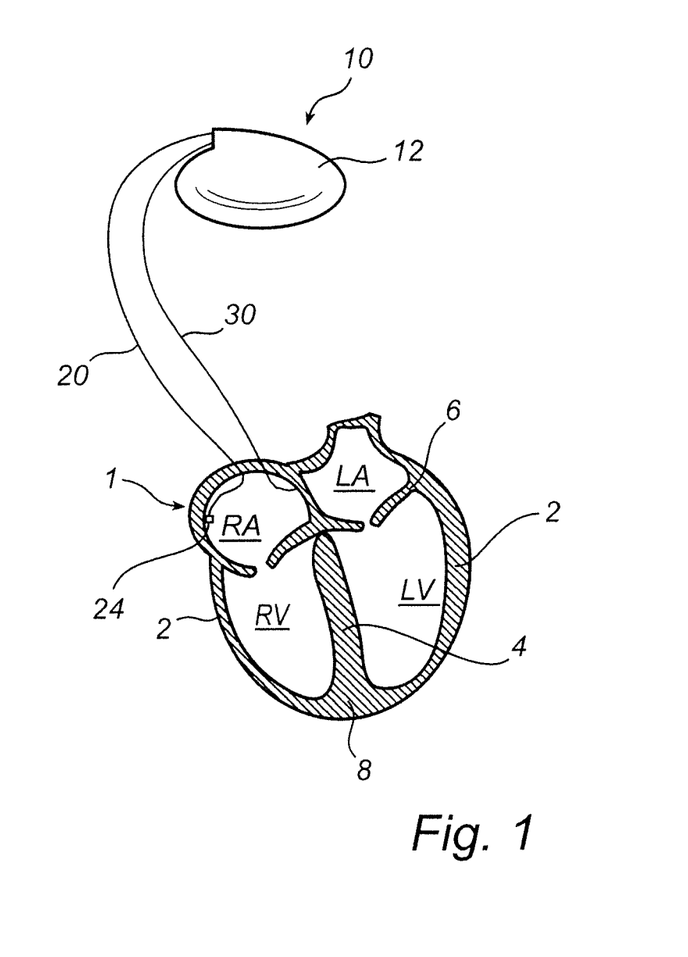
FIG. 1 is a simplified partly cutaway view illustrating an implantable stimulator including an electrode configuration according to the present invention.

In FIG. 1 an arrangement of a implantable pacing system 10 according to an embodiment of the present invention implanted in a patient (not shown), the pacing system 10 includes a subcutaneously disposed stimulation device or pacemaker 12. The stimulation device 12 is in electrical communication with a patient's heart 1 by way of two leads 20 and 30 suitable for delivering stimulation, which leads 20 and 30 are connectable to the stimulation device 12. The illustrated portions of the heart 1 include right atrium RA, the right ventricle RV, the left atrium LA, the left ventricle LV, cardiac walls 2, the ventricle septum 4, the valve plane 6, and the apex 8.

In order to provide stimulation therapy to the right atrium RA, the stimulation device 12 is coupled to an implantable right atrial lead 20 having at least one electrode 24, e.g. a tip electrode, adapted to placed or located in contact with the atrial wall. The electrode 24 is arranged for sensing electrical activity, intrinsic or evoked, in the right atrium RA.

In order to provide pacing to HIS bundle, the stimulation device 12 is coupled to a lead 30 designed to penetrate the endocardium from right atrium RA, so as to place at least one electrode (not shown) in contact with the HIS bundle. The lead 30 and the at least one electrode for stimulating the HIS bundle will be described in more detail below with reference to FIGS. 3 and 4. The HIS bundle electrode is capable of sensing HIS events as well as right ventricular events, such as a ventricular activation, since the period of time between a native HIS event or a paced HIS event to the subsequent ventricle contraction (activation) typically is about 70 msec.

The Bundle of HIS is reached from the atrium by mapping in the area of the Triangle of Koch. The correct region at which the endocardium should be penetrated with the lead in order to reach the Bundle of HIS is identified by finding the spot where the largest HIS Bundle potential is measured. The electrode arrangement, e.g. the lead helix, may then be fixated in this spot.

A physician implanting the medical system according to the present invention, may begin with implanting the lead 30 into the right atrium. The physician will then look for characteristics close to the AV node in order to locate a site where to place the electrode arrangement in the right atrium, which arrangement in this case is a rotable helix adapted to penetrate the myocardium. For example, by using a fluoroscope, the physician may look for the boundaries of the triangle of Koch, which contain HIS bundle at its apex. Upon locating this location the physician would implant the medical lead 30 in a location believed to be located down the electrical path of an improperly working portion of the intrinsic conduction system, i.e. the HIS bundle in this case. The physician then begins to stimulate the intrinsic conduction system. During the stimulation the different electrodes of the electrode arrangement is activated, for example, according to a predetermined scheme to determine an optimal electrode for pacing HIS bundle. Since the location of HIS bundle may vary in three dimensions, and which location also is different for every person, the physician hence selectively activates different electrodes of the electrode arrangement to determine an optimal conduction position for the particular patient. For each electrode at least one pacing measure or selection parameter is obtained to determine the function or the efficiency of the respective electrode. This or these pacing measure(-s) or selection parameters can be determined by a processing circuit of the implantable medical device based on, for example, measured surface ECG signals and/or measured stimulation responses (e.g. thresholds and/or sensing values), or by a processing circuit of an external programmer device connected to the implantable medical device or the medical lead. According to one embodiment, the surface ECG is obtained and the QRS complex and T-wave complex is identified in the surface ECG and when HIS bundle is reached, the QRS complex and T-wave complex should substantially correspond to a native QRS complex and a native T-wave complex with respect to morphology, including amplitude, configuration and duration being the result from an intrinsic event. This is described by Deshmukh et al, in Circulation 2000; 101; 869-877. According to another alternative, the period of time between a stimulation at the HIS bundle and the subsequent ventricular event (HIS-ventricular interval or H-V-interval) is determined and this period of time is compared with the period of time for a native stimulation, i.e. a spontaneous sensed event at HIS and the sensed ventricular event. When the HIS bundle is reached, the two periods of time should be substantially equal, i.e. the length of the respective periods of time should substantially coincide.

Figure 2:
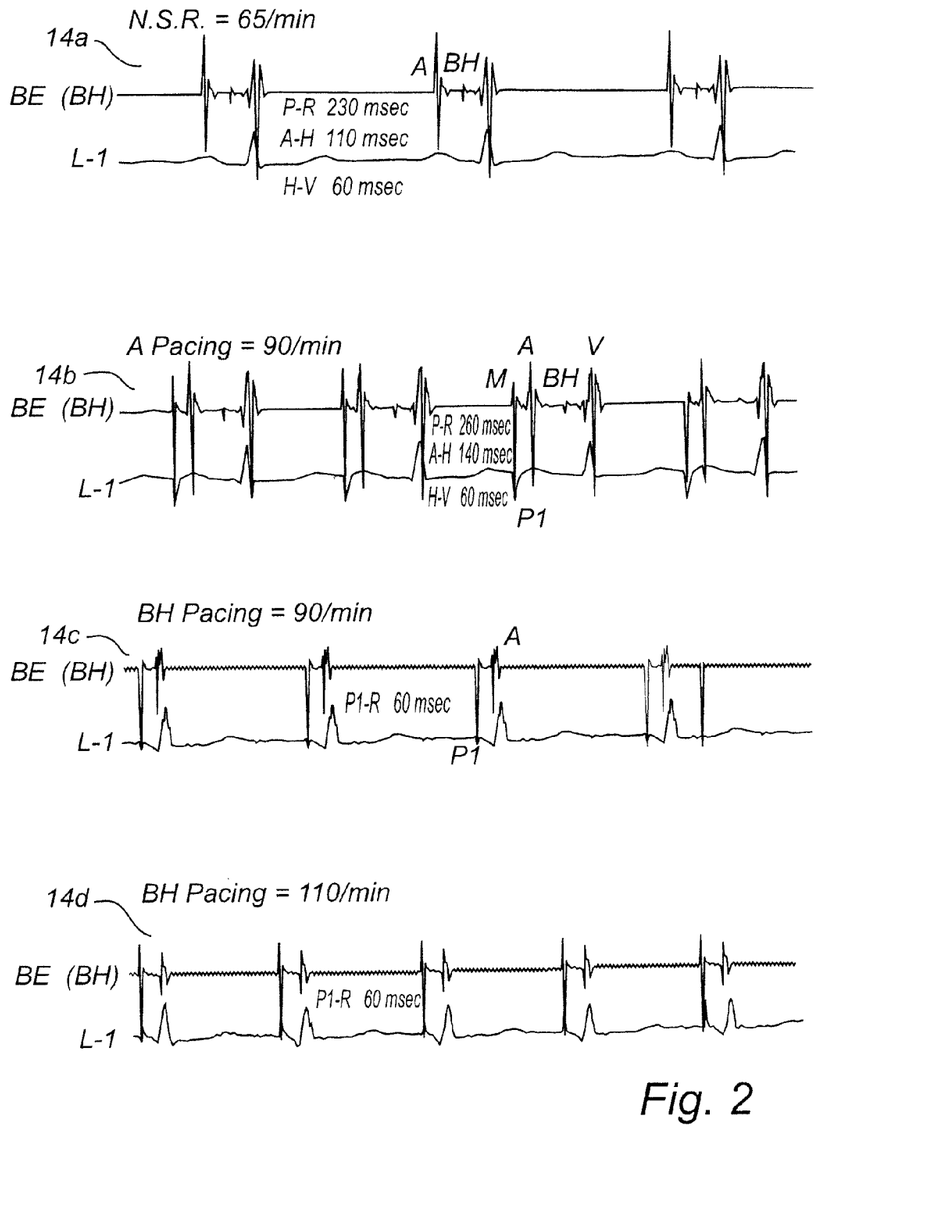
FIG. 2 illustrates simultaneous recordings of bipolar electrogram from the area of A-V junction and a standard ECG lead at normal sinus rhythm, atrial pacing an pacing at HIS bundle at different rates, respectively.

With reference to FIG. 2, recordings obtained during tests performed on patients that illustrate that pacing or stimulation at the HIS bundle, for example, low in atrial septum or high in the interventricular septum provides similar results as natural or intrinsic stimulation will be discussed. The waveforms referred to as 14a-14d shown in FIG. 2 illustrate simultaneous recording of bipolar electrogram (BE) from the area of A-V junction and a standard ECG lead (L1), respectively. BE (BH) represents bipolar electrogram from the area of the A-V junction, BE (RA) represents bipolar electrogram from the right atrium, L-I represents lead I of the standard lead electrogram, NSR represents normal sinus rhythm, A pacing represents atrial pacing, BH pacing represents pacing at bundle of HIS, PI represents pacing impulse, and PI-R represents the time interval from the pacing impulse to the onset of the QRS complex. The waveforms referred to as 14a show the recordings at normal sinus rhythm of 65 per minute. As can be seen, the A-H and H-V interval are 100 and 60 msec, respectively. From the waveform referred to as 14b, which illustrates atrial pacing at 90 per minute, it can be seen that the A-H interval was prolonged to 140 msec while the H-V-interval remained unchanged at 60 msec. In waveforms referred to as 14c and 14d, respectively, bundle of HIS pacing at rates of 90 and 110 per minute are shown, respectively. The pacing impulse (PI) to the onset of the QRS complex time (PI-R) remained constant at 60 msec during both levels of BH pacing rates, i.e. equal to the H-V-interval at normal sinus rhythm and at atrial pacing. Furthermore, it can also been seen that the shape or morphology of the QRS complex is similar to that during normal sinus rhythm, e.g. no substantial change in amplitude, configuration, and duration.

Figure 3:
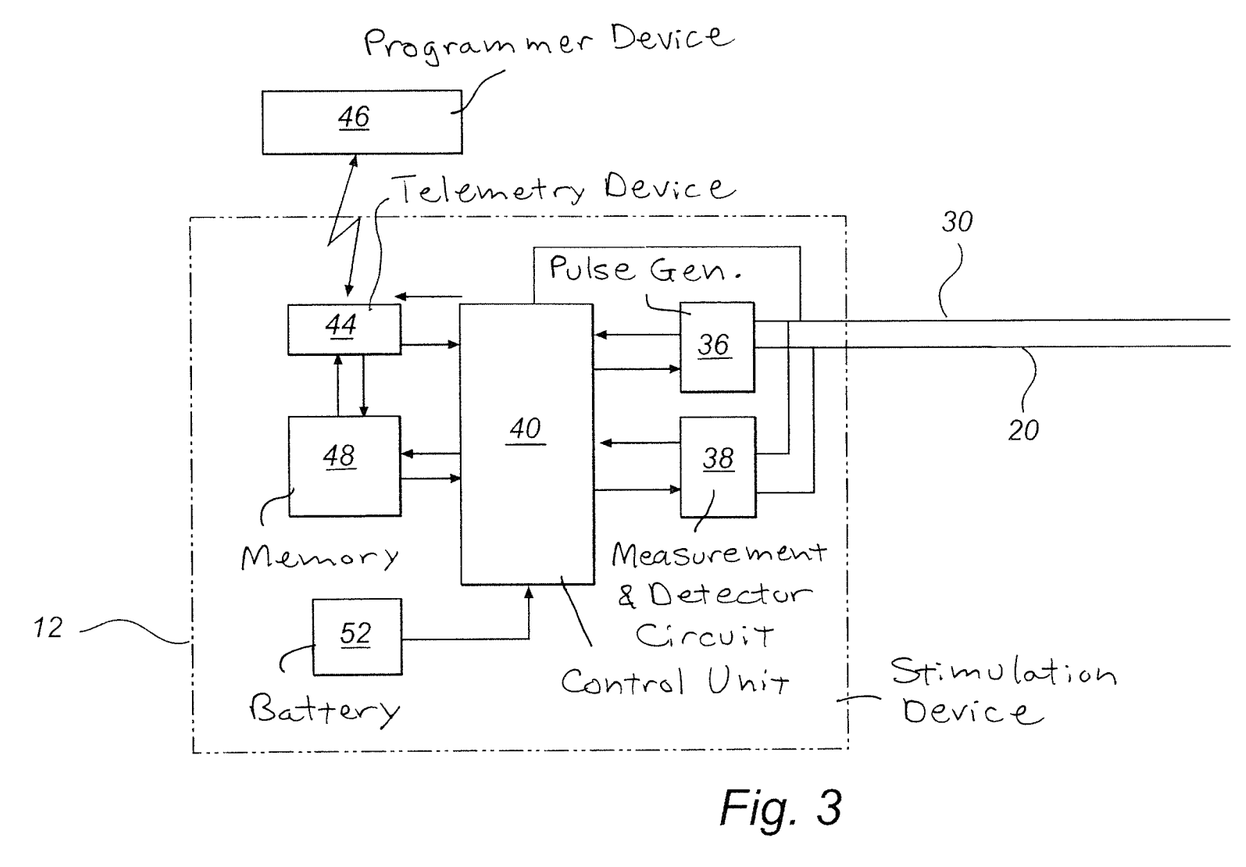
FIG. 3 is an illustration in block diagram form of a system according to an embodiment of the present invention including an implantable stimulator.

Turning now to FIG. 3, an embodiment of a implantable medical device, e.g. a stimulation device or a pacemaker according to the present invention will be discussed. FIG. 3 is a schematic block diagram of the stimulation device. For illustrative purposes, reference is made to FIG. 1 for the elements of the leads that are intended for positioning in or at the heart.

The stimulation device 12 is connected to a heart 1 order to sense heart signals and emit stimulation pulses to the heart 1. Electrodes located within and at the heart and outside the heart, for example, an indifferent electrode (which, in this instance, consists of the enclosure of the stimulation device 12 but can also consist of a separate electrode located somewhere in the body) are connected to a pulse generator 36 in the stimulation device 12. The electrodes located within are connected to the stimulation device 12 via leads, for example, the leads 20 and 30 shown in FIG. 1. A measurement and detector circuit 38 is also connected to the electrodes in order to sense activity of the heart.

The pulse generator 36 and the measurement circuit 38 are controlled by a control unit 40 which regulates the stimulation pulses with respect to amplitude, duration and stimulation interval, the sensitivity of the measurement circuit 38 etc.

The lead 30 includes a penetrating electrode arrangement (which will be described in more detail below with reference to FIGS. 4 and 5) in the distal end for enabling attachment of the lead to tissue. The penetrating electrode arrangement includes at least two electrodes electrically separated from each other. The electrodes can be selectively activated to deliver stimulation to a selected tissue site, i.e. the best electrode for stimulating HIS bundle can be selected. The electrodes are connected to the pulse generator 36 and the measurement circuit 38 via a selection device or a switching device 42 (see FIGS. 6 and 7), which will be discussed below with reference to FIGS. 4 and 5.

A control unit 40 controls the pulse generator 36, the measurement circuit 38, and, optionally, the selection device 42 via a data bus (not shown). The selection device 42 may, in some applications of the present invention, be controlled manually by the physician using, for example, an external device 46, for example a extracorporeal programmer device. The programmer device 46 may communicate with the implantable medical device 12 wirelessly via a telemetry unit 44 or via a physical connection. This may be the case, for example, during the implantation procedure. Using the telemetry unit 44, a physician may also program the control unit 40 to perform various functions via the programmer device 46.

The telemetry unit 44 is also connected to the data bus. Thus, the heart stimulator 12 can communicate, via the telemetry unit 44, with external devices 46, for example, an extracorporeal programmer, a home monitoring device, or a patient worn device via a communication network, for example, a wireless communication network including at least one external radio communication network such as wireless LAN ("Local Area Network"), GSM ("Global System for Mobile communications"), or UMTS ("Universal Mobile Telecommunications System"). For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. The notification may include at least the patient identity, the occurrence of a myocardial infarction and/or the location of the detected infarct within the heart. The communication unit may be adapted to communicate with the user equipment, e.g. mobile phone, a pager or a PDA ("Personal Digital Assistant"), which is adapted to receive the notification via, for example, Bluetooth and to transmit it via the communication network further on to the medical care institution.

Further, a memory circuit 48 is connected to the control unit 40, which memory circuit 48 may include a random access memory (RAM) and/or a non-volatile memory such as a read-only memory (ROM).

Power for the stimulation device 12 is supplied by a battery 52.

Figure 4:
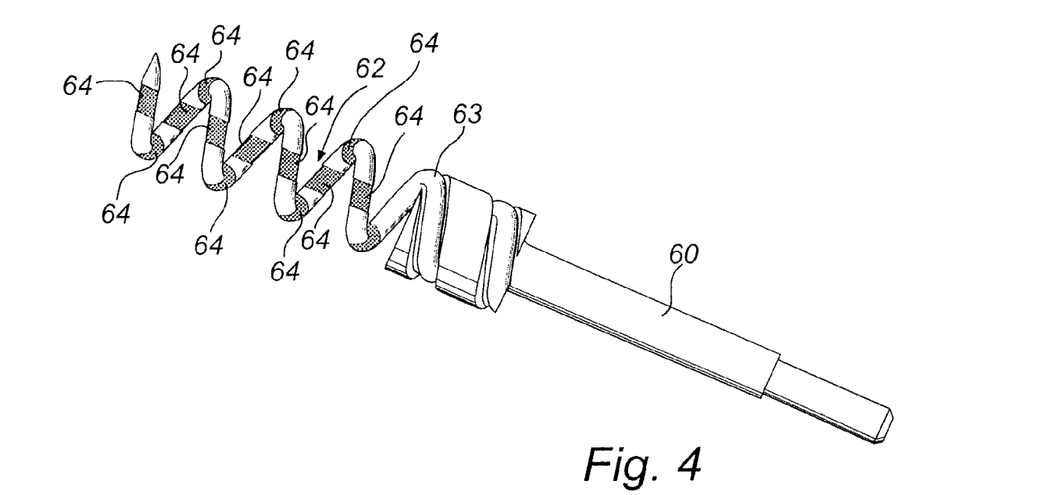
FIG. 4 is a schematic view of an penetrating electrode arrangement according to an embodiment of the present invention.

With reference now to FIG. 4, one embodiment of the penetrating electrode arrangement of the medical lead according to the present invention will be discussed. The lead 60 comprises a penetrating electrode arrangement 62 in the distal end for enabling attachment of the lead 60 to tissue. The penetrating electrode arrangement 62 includes a helix 63 comprising a number of individual electrodes 64a-m, or stimulating surfaces, electrically separated from each other. In this embodiment, the electrodes 64a-m are arranged as ring electrodes but, however, as the skilled person realizes the electrodes may be arranged as circular segments (e.g. a half circle or a quarter of a circle) instead of ring electrodes. The electrodes 64a-m can be selectively activated, i.e. individually addressed, to deliver stimulation to a selected tissue site, i.e. the best electrode for stimulating HIS bundle can be selected. The electrodes 64a-m are connected to the pulse generator 36 and the measurement circuit 38 via a selection device or a switching device 42, which will be described in more detail below with reference to FIG. 6, allowing each electrode 64a-m to be individually addressed. This embodiment of the electrode arrangement can be realized by means of a helix shaped plastic wire incorporating metallic conductors (not shown) which are isolated from each other by means of, for example, by the plastic wire or by a polymeric layer on each wire or conductor. In order to provide the electrodes 64a-m, the plastic insulation may be grinded away such that the conductors are exposed.

Figure 5:
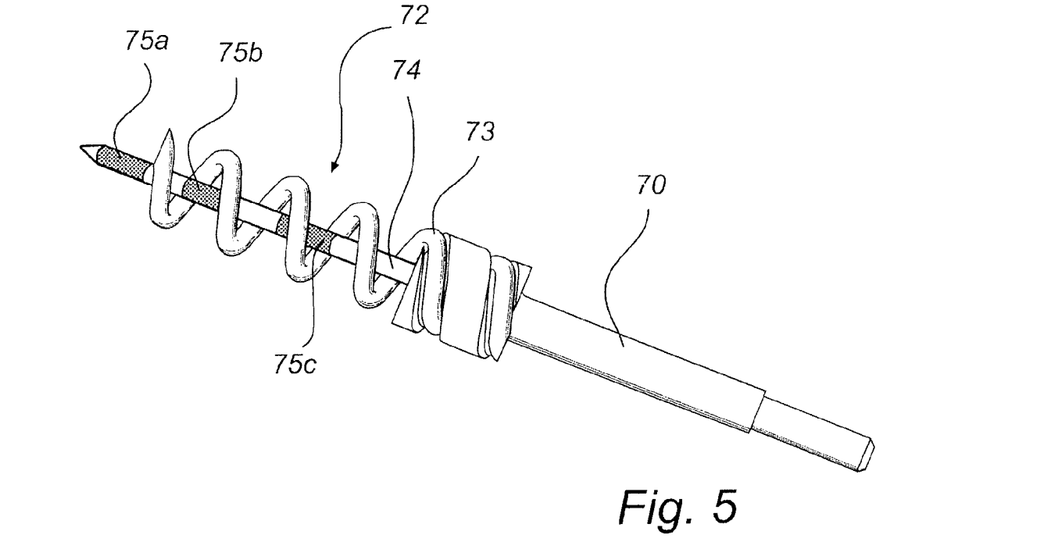
FIG. 5 is a schematic view of an penetrating electrode arrangement according to another embodiment of the present invention.

Turning now to FIG. 5, another embodiment of the penetrating electrode arrangement of the medical lead according to the present invention will be discussed. The lead 70 comprises a penetrating electrode arrangement 72 in the distal end for enabling attachment of the lead 70 to tissue. The penetrating electrode arrangement 72 includes helix 73 and nail-like pin 74 arranged within the helix 73. The pin 74 includes a number of individual electrodes 75a-c, or stimulating surfaces, electrically separated from each other. In this embodiment, the electrodes 75a-c are arranged as ring electrodes but, however, as the skilled person realizes the electrodes may be arranged as circular segments (e.g. a half circle or a quarter of a circle) instead of ring electrodes. The electrodes 75a-c can be selectively activated, i.e. individually addressed, to deliver stimulation to a selected tissue site, i.e. the best electrode for stimulating HIS bundle can be selected. The electrodes 75a-c are connected to the pulse generator 36 and the measurement circuit 38 via a selection device or a switching device 42, which will be described in more detail below with reference to FIG. 6, allowing each electrode 75a-c to be individually addressed. In this embodiment, the pin 74 may be a plastic wire incorporating metallic conductors (not shown) which are isolated from each other by means of, for example, by the plastic wire or by a polymeric layer on each wire or conductor. In order to provide the electrodes 75a-c, the plastic insulation can be grinded away such that the conductors are exposed.

Figure 6:
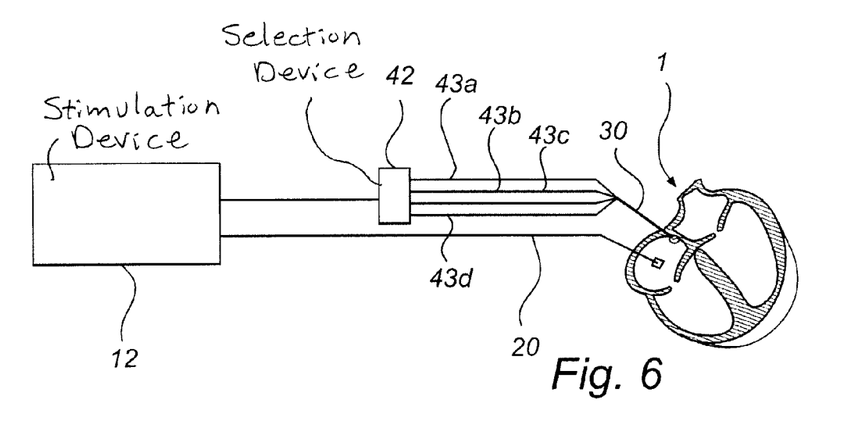
FIG. 6 is an illustration in block diagram form of a system according to another embodiment of the present invention including an implantable stimulator.
Figure 7:
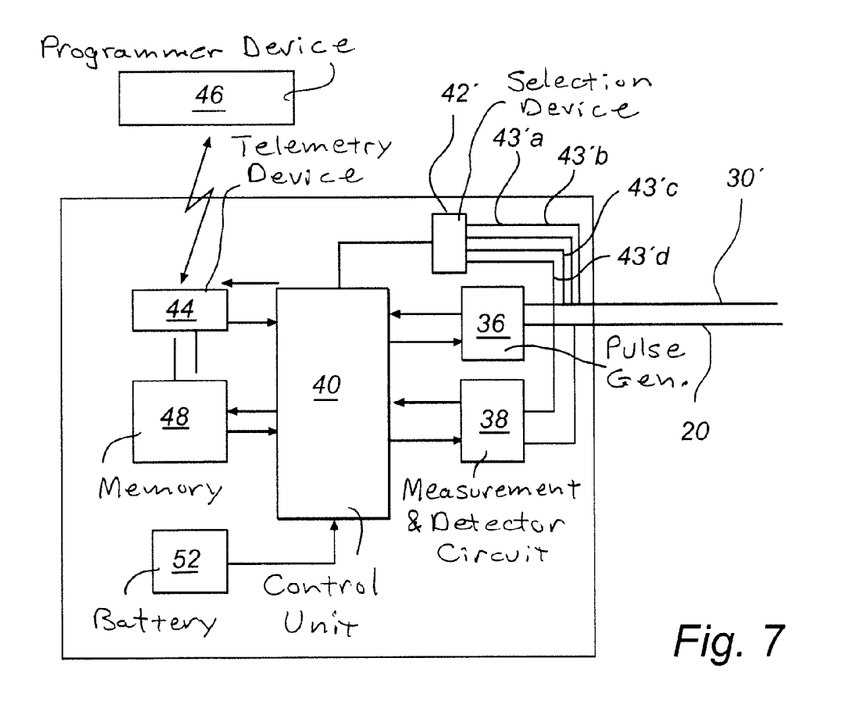
FIG. 7 is an illustration in block diagram form of a system according to a further embodiment of the present invention including an implantable stimulator.

Turning now to FIGS. 6 and 7, further embodiments of the present invention will be discussed. As can be seen in FIG. 6, the stimulation unit or pacemaker 12 is connected to the heart 1 by the medical leads 20, 30, respectively. The medical lead 30 is comprises a penetrating electrode arrangement in the distal end for enabling attachment of the lead to tissue, for example, the penetrating electrode arrangement as described above with reference to FIG. 4 or 5. As described above, the penetrating electrode arrangement includes a number of electrodes, or an electrode array, electrically separated from each other. The electrodes can be selectively activated to deliver stimulation to a selected tissue site, i.e. the best electrode for stimulating the HIS bundle can be selected. The electrodes are connected to the pulse generator 36 and the measurement circuit 38 via the selection device or a switching device 42, which is arranged at or in the medical lead 30. The operation of the selection device 42 is controlled by the control unit 40. The selection device 42 may, for example, be implemented as switch. A number of conductors 43a-43d is connected to a respective electrode surface of the penetrating electrode arrangement. In FIG. 6 only four conductors are shown, but, as the skilled person realizes, this number of conductors may be adapted to the number of electrode surfaces of the penetrating electrode arrangement such that each electrode surface is connected to the selection device 42 by means of a respective conductor.

In FIG. 7, an alternative embodiment of the present invention is shown where the selection device 42' is arranged in the stimulation device 12' in connection with the control unit 40 and the medical lead 30'. A number of conductors 43'a-d is connected to a respective electrode surface of the penetrating electrode arrangement. In FIG. 6 only four conductors are shown, but, as the skilled person realizes, this number of conductors may be adapted to the number of electrode surfaces of the penetrating electrode arrangement such that each electrode surface is connected to the selection device 42' by means of a respective conductor.

Figure 8:
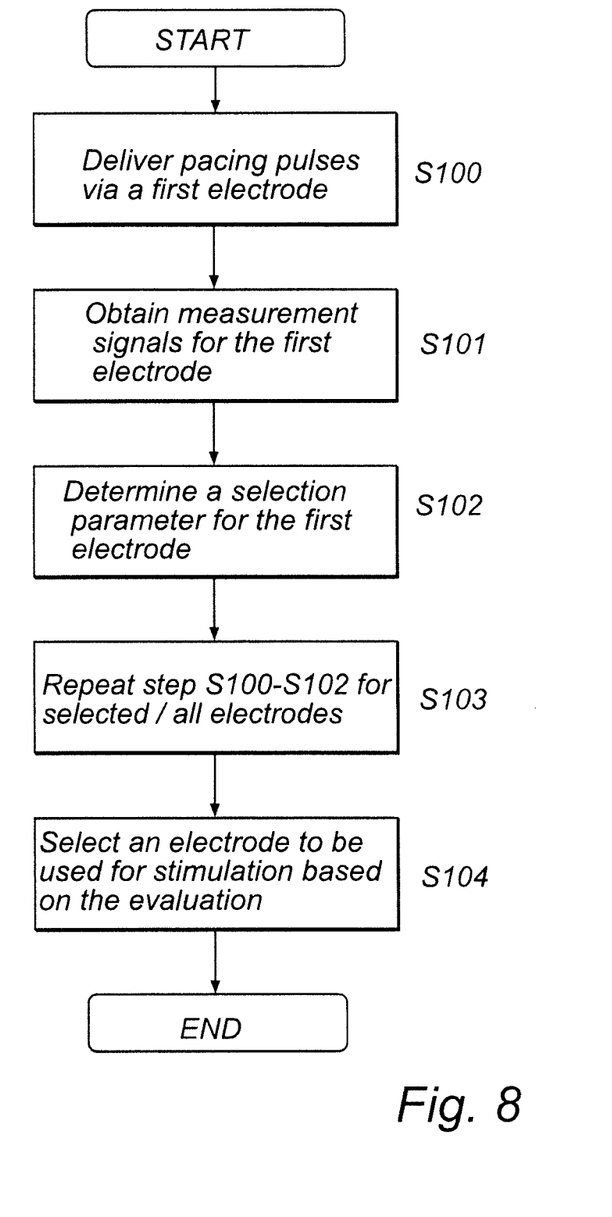
FIG. 8 is a schematic flow chart illustrating the principles of the method according to the present invention.

Referring now to FIG. 8, an embodiment of the method for delivering pacing pulses to HIS bundle of a heart of a patient according to the present invention will be discussed. First at step S100, pacing pulses is delivered to the heart via a medical lead adapted to be attached with a distal end to tissue of the heart, the medical lead including a penetrating electrode arrangement in the distal end for enabling attachment of the lead to tissue and at least two electrodes arranged on the electrode arrangement being electrically separated from each other, each being connected to the at least one conductor. In FIGS. 4 and 5, two alternative embodiment of the electrode arrangement including electrodes are shown. A selection device is controlled to selectively activate at least one of the electrodes. If this method is performed at an implantation, the physician may select a first electrode to be activated. The electrode may also be selected automatically, for example, in accordance with a predetermined scheme, which may be the case if a post-implant optimization procedure is performed. Then, at step S102, surface ECG signals or IEGM signals corresponding to a physiological activity of the heart and/or measurement signals corresponding to the operation of the electrode are obtained. These signals may be obtained for a predetermined number of consecutive cardiac cycles. The obtained signal may also be processed, for example, an average value may be calculated over the measured cardiac cycles. Thereafter, at step S104, at least one selection parameter or pacing measure based on an evaluation of the obtained surface ECG signals or IEGM signals and/or the measurement signals is determined.

At an implantation, at least one pacing measure or selection parameter is obtained to determine the function or the efficiency of the respective electrode. This or these pacing measure(-s) or selection parameters can be determined by a processing circuit of the implantable medical device based on, for example, measured surface ECG signals and/or measured stimulation responses (e.g. thresholds and/or sensing values), or by a processing circuit of an external programmer device connected to the implantable medical device or the medical lead. According to one embodiment, the surface ECG is obtained and the QRS complex and T-wave complex is identified in the surface ECG and when HIS bundle is reached, the QRS complex and T-wave complex should substantially correspond to a native QRS complex and a native T-wave complex with respect to morphology, including amplitude, configuration and duration being the result from an intrinsic event. This is described by Deshmukh et al, in Circulation 2000; 101; 869-877. According to another alternative, the period of time between a stimulation at HIS bundle and the subsequent ventricular event (HIS-ventricular interval or H-V-interval) is determined and this period of time is compared with the period of time for a native stimulation, i.e. a spontaneous sensed event at HIS and the sensed ventricular event. When the HIS bundle is reached, the two periods of time should be substantially equal, i.e. the length of the respective periods of time should substantially coincide. This alternative is also suitable to use during at a follow-up at the hospital when the patient visits his/her physician.

At step S106, the steps S100, S102, and S104 may be repeated for all electrodes of the electrode arrangement, or for selected electrodes. Subsequently, at step S108, the selection device is controlled to selectively activate the electrode providing the best HIS bundle simulation based on the at least one selection parameter, as indicated above. However, as the skilled person realizes, the embodiment described with reference to FIG. 8 is only exemplifying and there is a number of conceivable alternative methods. For example, one electrode at a time can be used and evaluated and when the selection parameter(-s) predetermined conditions with regard to, for example, conduction time from HIS bundle to ventricular activation are satisfied, the procedure is stopped and the electrode providing the satisfying result is selected for stimulation.

If this method is performed in the chronic state, i.e. post-implantation, the morphology and/or H-V-interval from sensed native events at the bundle of HIS and subsequent sensed ventricular activation obtained from the IEGM (intracardiac electrogram) can be compared with a predetermined reference morphology and/or predetermined reference H-V-interval. The reference morphology and reference H-V interval are preferably obtained from the same patient, i.e. the morphology and/or H-V-interval from sensed native events at the bundle of HIS and subsequent sensed ventricular activation are recorded. A deviation from the predetermined reference morphology and/or predetermined reference H-V-interval may be used as trigger for an automatic test procedure for identifying a more suitable electrode. In another embodiment for post-implant optimization, the morphology and/or H-V-interval from stimulated events at the bundle of HIS and subsequent sensed ventricular activation obtained from the IEGM (intracardiac electrogram) can be compared with a predetermined reference morphology and/or predetermined reference H-V-interval. The reference morphology and reference H-V interval are preferably obtained from the same patient, i.e. the morphology and/or H-V-interval from stimulated events at the bundle of HIS and subsequent sensed ventricular activation are recorded. A deviation from the predetermined reference morphology and/or predetermined reference H-V-interval may be used as trigger for an automatic test procedure for identifying a more suitable electrode.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

We claim as our invention:

1. A medical system for delivering pacing pulses to HIS bundle of a heart of a patient when implanted in said patient, said system comprising:
   a medical lead, which is adapted to be fixated to tissue of said heart, said medical lead including
      a lead body including a flexible insulating tubing and at least one conductor arranged within said tubing;
      a penetrating electrode arrangement coupled to a distal end of the medical lead, the penetrating electrode arrangement including a fixation apparatus adapted to fixate the lead to the tissue of said heart; and
      at least two electrodes arranged on said fixation apparatus, wherein the at least two electrodes are electrically separated from each other and wherein the at least two electrodes are electrically coupled to said at least one conductor; and
   a selection device connected to the at least two electrodes and being adapted to selectively activate at least one of said electrodes, and an implantable medical device configured to be coupled to said medical lead, said medical device comprising a pacing circuit adapted to deliver said pacing pulses to said heart via said selection device and said medical lead.

2. The medical system according to claim 1, wherein said system further comprises an extracorporeal programmer device being adapted to control said selection device.

3. The medical system according to claim 2, wherein said programmer device further comprises a processing device configured to control said selection device to selectively activate at least one of said electrodes to direct said pacing pulses to HIS bundle, said processing device is adapted to control said selection device to selectively activate at least one of said electrodes by connecting said at least one electrode with said pacing circuit based on at least one selection parameter.

4. The medical system according to claim 3, wherein said programmer device further is configured to obtain ECG or IEGM signals corresponding to a physiological activity of said heart and/or measurement signals corresponding to the operation of said electrodes from said measurement circuit.

5. The medical system according to claim 4, wherein said processing device is adapted to determine said at least one selection parameter based on an evaluation of said obtained ECG, said IEGM signals and/or said measurement signals.

6. The medical system according to claim 1, wherein said medical device further comprises a processing device adapted to control said selection device to selectively activate at least one of said electrodes to direct said pacing pulses to the HIS bundle, said processing device being configured to control said selection device to selectively activate at least one of said electrodes by connecting said at least one electrode with said pacing circuit based on at least one selection parameter.

7. The medical system according to claim 6, wherein said processing circuit is adapted to instruct said selection circuit, during a test procedure, to activate said electrodes according to a predetermined scheme, evaluate selection parameters obtained during a pacing period for each respective electrode to determine which electrode to use for HIS bundle pacing, and instruct said selection circuit to activate said determined electrode for HIS bundle pacing.

8. The medical system according to claim 1, wherein said implantable medical device further comprises a measurement circuit adapted to obtain IEGM signals corresponding to a physiological activity of said heart and/or measurement signals corresponding to the operation of said electrodes.

9. The medical device according to claim 8, wherein said processing circuit is configured to determine a conduction time from a sensed native HIS bundle event or from a delivery of at least one pacing pulse to His bundle to a subsequent ventricular activation using said IEGM signals; and instruct said selection circuit to initiate said test procedure if said determined conduction time exceeds a predetermined reference threshold.

10. The medical system according to claim 8 wherein said measurement circuit is adapted to determine a morphology of a QRS complex for respective consecutive cardiac events using said IEGM signals, and wherein said processing circuit is configured to evaluate said determined QRS complex to determine whether it satisfies predetermined conditions; and instruct said selection circuit to initiate a test procedure if said determined QRS complex do not satisfies said predetermined conditions.

11. The medical system according to claim 1, wherein said selection device is arranged in said medical device, or wherein said selection device is arranged in said medical lead.

12. The medical system according to claim 1, wherein said fixation apparatus includes a rotatable helix adapted for enabling an attachment of the lead to tissue by screwing the helix into the tissue, said helix comprising said at least two electrodes or wherein said fixation apparatus includes a rotatable helix adapted for enabling an attachment of the lead to tissue by screwing the helix into the tissue and an penetrating pin comprising said at least two electrodes, said penetrating pin being arranged such that said helix partly encircles said pin.

13. A method for delivering pacing pulses to the HIS bundle of a heart of a patient, said method comprising:
    delivering pacing pulses to said heart via a medical lead, the medical lead being adapted to be fixated to tissue of said heart, said medical lead including
        a lead body including a flexible insulating tubing and at least one conductor arranged within said tubing;
        a penetrating electrode arrangement coupled to the distal end of the lead, the penetrating electrode arrangement including a fixation apparatus for enabling fixation of the lead to tissue; and
        at least two electrodes arranged on said fixation apparatus, wherein the at least two electrodes are electrically separated from each other and wherein the at least two electrodes are each electrically coupled to said at least one conductor; and
    controlling a selection device to selectively activate at least one of said electrodes to direct pacing pulses to HIS bundle.

14. The method according to claim 13, wherein said step of controlling comprises controlling said selection device to selectively activate at least one of said electrodes based on at least one selection parameter.

15. The method according to claim 13, further comprising the steps of:
    obtaining surface ECG or IEGM signals corresponding to a physiological activity of said heart and/or measurement signals corresponding to the operation of said electrodes, and determining said at least one selection parameter based on an evaluation of said obtained surface ECG or IEGM signals and/or said measurement signals.

16. The method according to claim 13, further comprising the steps of:
    instructing said selection circuit, during a test procedure, to activate said electrodes according to a predetermined scheme, evaluating selection parameters obtained during a pacing period for each respective electrode to determine which electrode to use for HIS bundle pacing, and instructing said selection circuit to activate said determined electrode for HIS bundle pacing.

17. The method according to claim 16, further comprising the steps of:
    determining a conduction time from a sensed HIS bundle event or from delivery of at least one pacing pulse to His bundle to a ventricular activation using said surface ECG or said IEGM signals, and instructing said selection circuit to initiate said test procedure if said determined conduction time exceeds a predetermined reference threshold.

18. The method according to claim 17 comprising: determining a morphology of a QRS complex for respective consecutive cardiac events using said surface ECG or said IEGM signals, evaluating said determined QRS complex to determine whether it satisfies predetermined conditions; and instructing said selection circuit to initiate said test procedure if said determined QRS complex do not satisfies said predetermined conditions.

19. An implantable medical system for delivering pacing pulses to the HIS bundle of a heart of a patient when implanted in said patient, said implantable medical system comprising:
   an implantable medical device comprising a pacing circuit adapted to produce said pacing pulses;
   an medical lead being adapted to be fixated to tissue of said heart and including
      a lead body including a flexible insulating tubing and at least one conductor arranged within said tubing;
   a penetrating electrode arrangement coupled to a distal end of the conductor, the penetrating electrode arrangement comprising a rotatable helix adapted for enabling fixation of the lead to tissue by screwing the helix into the tissue, said helix comprising; at least two electrodes arranged on said helix, wherein the at least two electrodes are electrically separated from each other, and wherein said at least two electrodes can be selectively activated to direct said pacing pulses to HIS bundle.

20. The medical lead according to claim 19, further comprising a selection device connected between a pacing circuit of said implantable medical device and said electrodes, said selection device being adapted to selectively activate at least one of said electrodes.

21. The medical lead according to claim 20, wherein said penetrating electrode arrangement includes a rotatable helix adapted for enabling an attachment of the lead to tissue by screwing the helix into the tissue, said helix comprising said at least two electrodes or wherein said penetrating electrode arrangement includes a rotatable helix adapted for enabling an attachment of the lead to tissue by screwing the helix into the tissue and an penetrating pin comprising said at least two electrodes, said penetrating pin being arranged such that said helix partly encircles said pin.

22. A medical system for delivering pacing pulses to HIS bundle of a heart of a patient when implanted in said patient, the system comprising:
   a medical lead comprising a lead body including a flexible insulating tubing and at least one conductor arranged within the tubing and a penetrating electrode arrangement coupled to a distal end of the medical lead, the penetrating electrode arrangement comprising a rotatable helix adapted to fixate the lead to tissue by screwing the helix into the tissue and a penetrating pin being arranged such that said helix partly encircles said pin and at least two electrodes arranged on the penetrating electrode arrangement, wherein the at least two electrodes are electrically separated from each other and wherein the at least two electrodes can be selectively activated to direct the pacing pulses to HIS bundle; and
   an implantable medical device configured to be coupled to the medical lead, the medical device including a pacing circuit adapted to deliver pacing pulses to the heart.

* * * * *